United States Patent
Hsieh

(10) Patent No.: US 9,117,304 B2
(45) Date of Patent: Aug. 25, 2015

(54) SYSTEM AND METHOD FOR IMPROVED SPATIAL RESOLUTION OF A MULTI-SLICE IMAGING SYSTEM

(71) Applicant: General Electric Company, Schenectady, NY (US)

(72) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 209 days.

(21) Appl. No.: 13/955,304

(22) Filed: Jul. 31, 2013

(65) Prior Publication Data

US 2015/0036794 A1 Feb. 5, 2015

(51) Int. Cl.
*A61B 6/00* (2006.01)
*G06T 11/00* (2006.01)
*A61B 6/03* (2006.01)
*G06T 7/00* (2006.01)

(52) U.S. Cl.
CPC ............... *G06T 11/008* (2013.01); *A61B 6/03* (2013.01); *G06T 7/0012* (2013.01); *G06T 2207/10081* (2013.01); *G06T 2207/20172* (2013.01); *G06T 2207/30004* (2013.01); *G06T 2211/416* (2013.01)

(58) Field of Classification Search
CPC ..................... A61B 6/032; G06T 2207/30004; G06T 7/0012; G06T 2207/10081; G06T 2207/10116; G06T 2207/20172
USPC .................................. 378/4–20; 382/128–131
See application file for complete search history.

(56) References Cited

U.S. PATENT DOCUMENTS

| | | | |
|---|---|---|---|
| 6,366,637 B1 | 4/2002 | Hsieh et al. | |
| 6,792,151 B1 | 9/2004 | Barnes et al. | |
| 6,798,860 B1 | 9/2004 | Hsieh et al. | |
| 8,135,186 B2 | 3/2012 | Bouman et al. | |
| 2010/0150421 A1 | 6/2010 | Nakanishi et al. | |
| 2011/0081071 A1 | 4/2011 | Benson et al. | |
| 2011/0200241 A1 | 8/2011 | Roy et al. | |

*Primary Examiner* — Courtney Thomas
(74) *Attorney, Agent, or Firm* — Ziolkowski Patent Solutions Group, SC

(57) ABSTRACT

A system and method include acquisition of a set of projections from an object using a CT imaging system and reconstruct an initial image of the scanned object from the set of projections, the reconstructed initial image comprising a plurality of pixels. The system and method also include identification of a candidate pixel within the plurality of pixels, application of a nonlinear enhancement to the candidate pixel to iteratively adjust an intensity value of the candidate pixel, and generation of a final image using the adjusted intensity value of the candidate pixel.

20 Claims, 10 Drawing Sheets

SYSTEM AND METHOD FOR IMPROVED SPATIAL RESOLUTION OF A MULTI-SLICE IMAGING SYSTEM

BACKGROUND OF THE INVENTION

Embodiments of the invention relate generally to diagnostic imaging and, more particularly, to a system and method for improved spatial resolution of a multi-slice imaging system.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. In particular, an x-ray tube included in the x-ray source emits the x-ray beam at a focal point or focal spots. The beam, after being attenuated by the subject, impinges upon an array of radiation or x-ray detectors.

In known CT systems, the x-ray beam is projected from the x-ray source through a pre-patient collimator that defines the x-ray beam profile in the patient axis, or z-axis. The collimator typically includes an x-ray-absorbing material with an aperture therein for restricting the x-ray beam.

X-ray detectors also typically include a collimator for collimating x-ray beams received at the detector, a scintillator for converting x-rays to light energy adjacent the collimator, and photodiodes for receiving the light energy from the adjacent scintillator and producing electrical signals therefrom. Alternatively, x-ray detectors may include a direct conversion device that convert x-ray beams directly to electrical signals.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for calibration and image reconstruction.

The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject so that the angle at which the x-ray beam intersects the subject is constantly changing. A group of x-ray attenuation measurements, i.e., projection data, from the detector array at one gantry angle is referred to as a "view". A "scan" of the subject comprises a set of views made at different gantry angles or view angles, during one revolution of the x-ray source and detector. Alternatively, an array of x-ray source and detector can be arranged to completely surround the patient, thereby permitting the CT system to acquire a complete set of data or projections without rotational movement.

The resolution of a CT imaging system along its z-axis is an important performance parameter. The ability to resolve fine structures enables improved diagnosis. For example, improved resolution aids not only in IAC and extremity studies, but also for cardiac applications to inspect the integrity of stent structures.

CT imaging systems typically provide image resolution along the patient long axis (z-axis) within limits imposed by such factors as collimator aperture size, x-ray focal spot size, detector cell size, and geometry of the CT system. A minimum slice thickness for at least one known CT system is 1.25 millimeters, as determined primarily by detector element pitch size. In order to improve image resolution, it is desirable to reduce slice thickness to less than 1 millimeter, and to achieve such reduction with minimal impact on imaging system hardware. For CT systems with native slice thickness less than 1 mm (e.g., at least one known CT system provides 0.625 mm), it is desirable to reduce the slice thickness even further (e.g., to less than 0.5 mm).

To reduce slice thickness of a single-slice or dual-slice imaging system, portions of the detector element are irradiated and the image data, such as projection data or image data, is deconvolved, to reduce the full-width-at-half maximum (FWHM) interval of the reconstructed slice profile. Difficulties can arise, however, in implementing this approach for a multi-slice imaging system collecting more than two detector row signals simultaneously because it is very difficult to design a pre-patient collimator to partially block the x-ray beam for each individual detector row.

Past efforts at improving spatial resolution in the z-axis for multi-slice imaging systems have focused primarily on hardware solutions, such as dicing the detector cells smaller or dynamically deflecting the x-ray focal spot to achieve improved sampling. Another approach that has been proposed for improving spatial resolution in the z-axis is the "thin twin" approach, in which a multi-slice detector is combined with a narrowly collimated x-ray beam to achieve thinner slice profiles than the aperture of the detector. Although these hardware-based approaches may improve resolution, these approaches increase the overall system costs, the complexity of the technology, and the acquisition time of the scanner.

Software-based solutions have also been proposed for improving z-axis spatial resolution. For example, various attempts have been made to use de-convolution techniques to reduce the slice sensitivity profile. Although these techniques may be effective in reducing the FWHM of the slice sensitivity profile, the techniques generally cause overshoot and undershoot in the processed images as a result of the characteristics of the de-convolution algorithms. The overshoot and undershoot phenomenon is highly undesirable, as it produces faulty structures around high-density objects and can potentially lead to clinical misinterpretation of the images.

Therefore, it would be desirable to design a system and method for improving spatial resolution in the z-axis of a multi-slice CT imaging system that overcomes the aforementioned drawbacks.

BRIEF DESCRIPTION OF THE INVENTION

In accordance with one aspect of the invention, a non-transitory computer readable storage medium has stored thereon a computer program comprising instructions, which, when executed by a computer, cause the computer to acquire a set of projections from an object using a CT imaging system and reconstruct an initial image of the scanned object from the set of projections, the reconstructed initial image comprising a plurality of pixels. The instructions also cause the computer to identify a candidate pixel within the plurality of pixels, apply a nonlinear enhancement to the candidate pixel to iteratively adjust an intensity value of the candidate pixel, and generate a final image using the adjusted intensity value of the candidate pixel.

In accordance with another aspect of the invention, a method of generating a CT image includes acquiring CT data representing an object from a CT imaging system, reconstructing a CT image from the acquired CT data, and identifying a set of candidate pixels from the CT image based on an intensity variation between neighboring pixels of the CT image. The method also includes iteratively enhancing an intensity of the set of candidate pixels and generating a final image of the object using the iteratively enhanced set of candidate pixels and a plurality of non-enhanced pixels from the CT image.

In accordance with another aspect of the invention, a CT system includes a rotatable gantry having an opening to receive an object to be scanned, an x-ray source positioned on the rotatable gantry and configured to project x-rays at the object, and a multi-slice detector array attached to the gantry and positioned to receive x-rays from the x-ray source that pass through the object. The CT system also includes a table positioned in the opening, the table moveable in a z-direction of the CT system and a computer. The computer is programmed to acquire a plurality of projection datasets of the object, reconstruct an image of the object using the plurality of projection datasets, and identify a plurality of candidate pixels from the reconstructed image based on an intensity variation between a respective candidate pixel of the plurality of candidate pixels and at least two pixels of the reconstructed image adjacent the respective candidate pixel. The computer is further programmed to modify an intensity of the plurality of candidate pixels and generate an enhanced image using the modified intensity of the plurality of candidate pixels.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. In addition, while embodiments of the invention are described with respect to image reconstruction techniques for use with CT systems, one skilled in the art will recognize that the concepts set forth herein are not limited to CT and can be applied to reconstruction techniques used with other imaging modalities in both the medical field and non-medical field, such as, for example, an x-ray system, a PET system, a SPECT system, an MR system, or any combination thereof. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
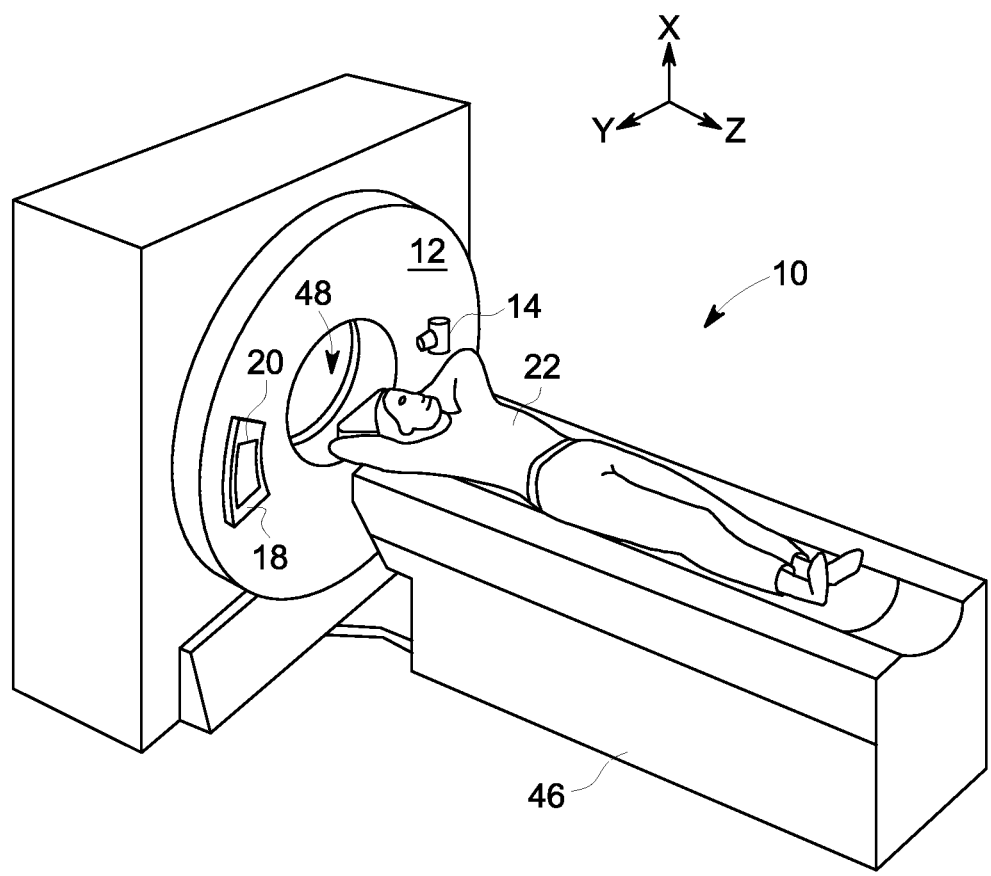
FIG. 1 is a pictorial view of a CT imaging system.
Figure 2:
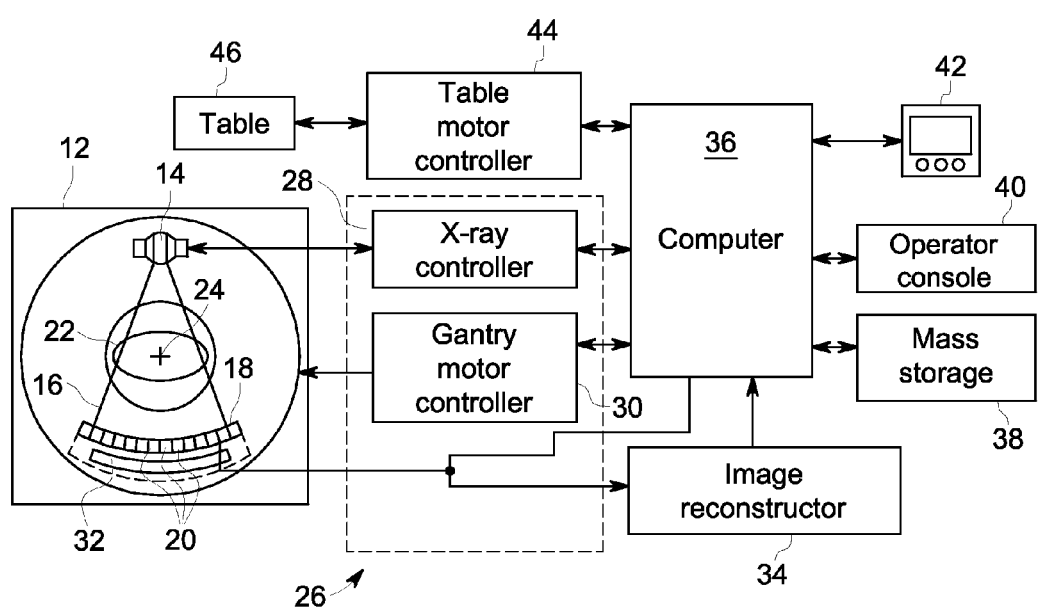
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor or computer processor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part along a z-axis or z-direction of the CT system 10.

Figure 3:
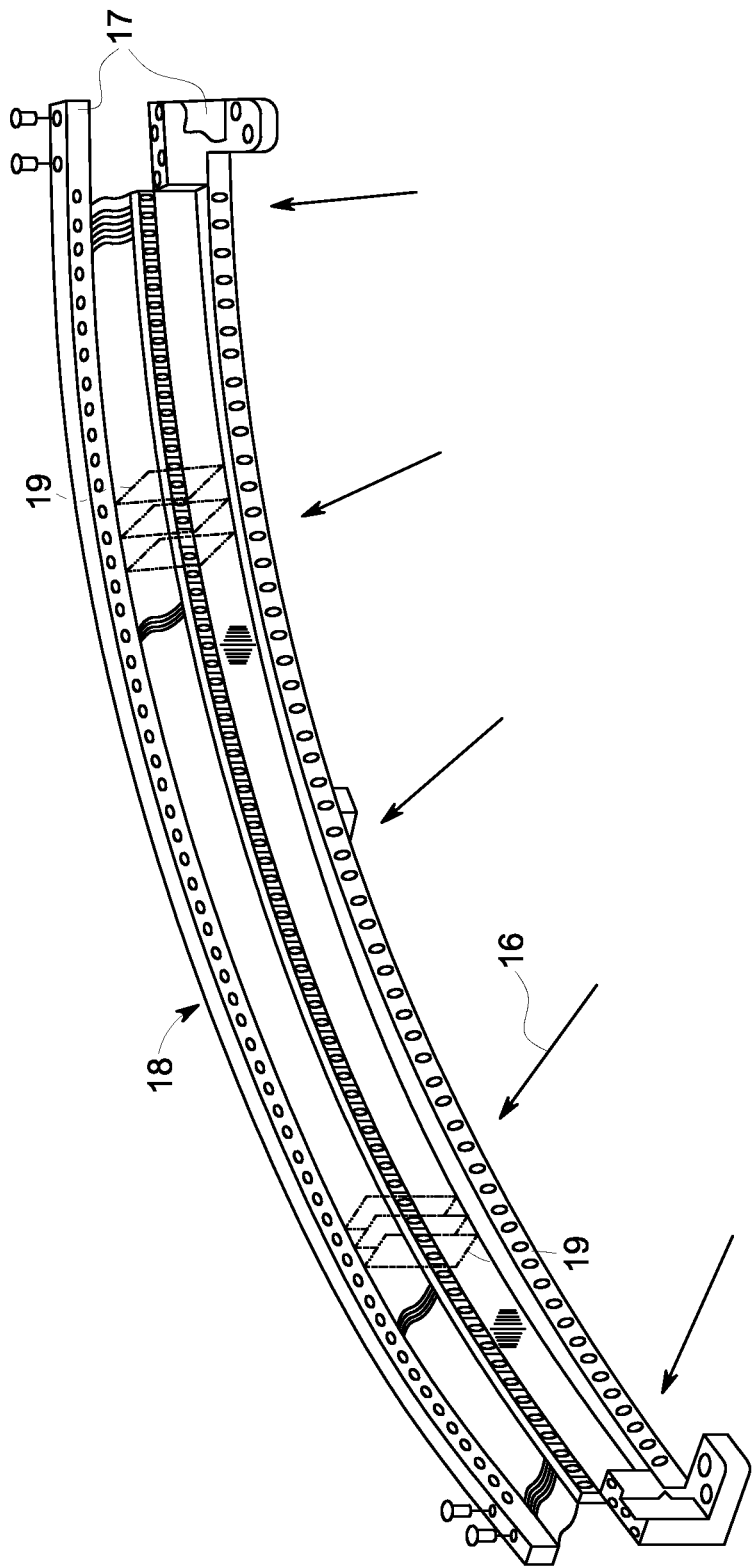
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detector modules 20, each detector module 20 having an array size of 64×16 of pixel elements 50. As a result, detector assembly 18 has 64 rows and 912 columns (57 detector modules) which allows 64 simultaneous slices of data to be collected with each rotation of gantry 12.

Figure 4:
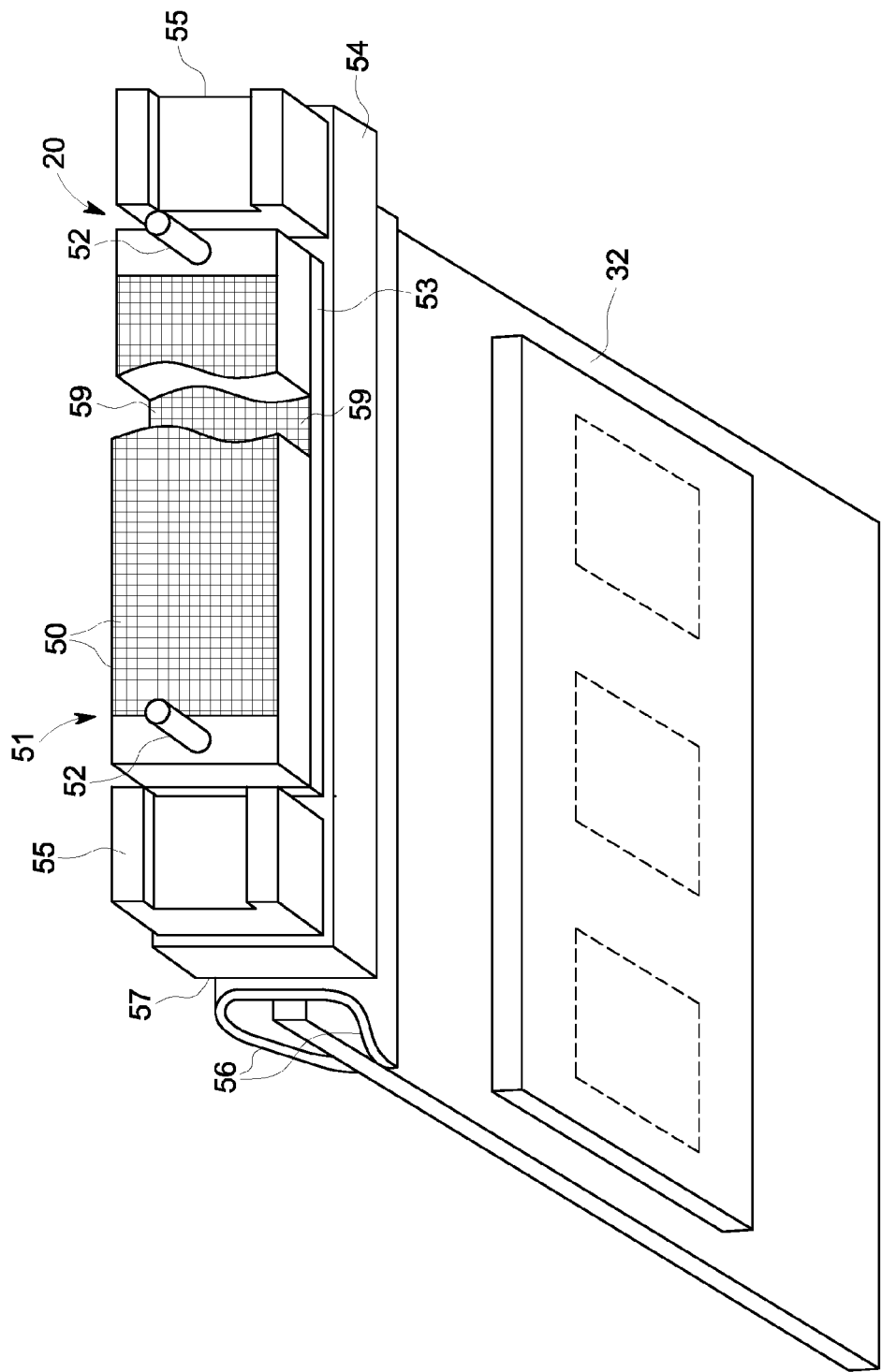
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an optical signal which is detected on a diode within backlit diode array 53. The analog signal generated is carried through multi-layer substrate 54, through flex circuits 56, to DAS 32 wherein the analog signal is converted to a digital signal.

Figure 5:
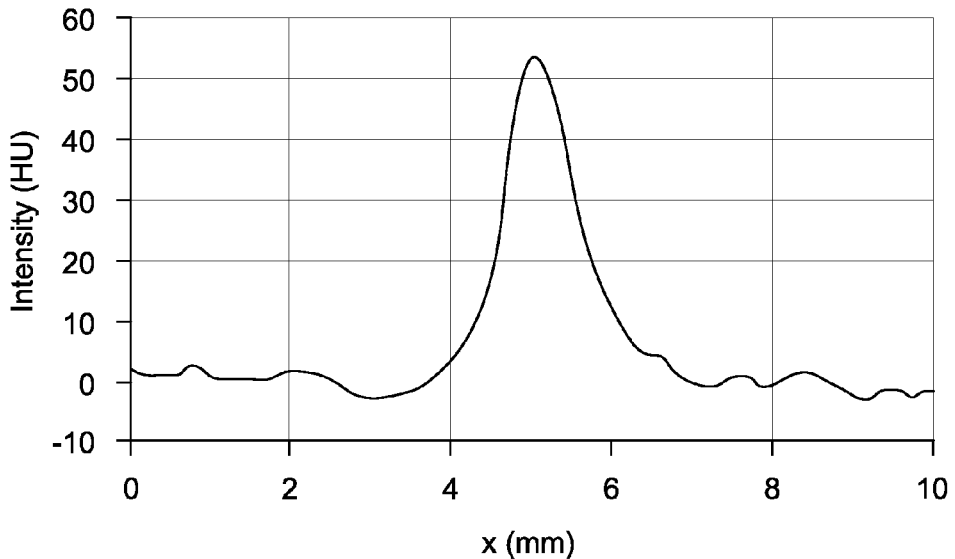
FIG. 5 is an exemplary slice sensitivity profile of a CT imaging system, such as the CT imaging system of FIG. 1.

FIG. 5 illustrates an exemplary slice sensitivity profile (SSP) 70 of a CT imaging system, such as CT system 10 of FIG. 1, operating in a helical scan mode. Exemplary SSP 70 was acquired with a helical pitch of 0.516 (33/64) and a targeted reconstruction thickness of less than 1 mm (i.e., sub-mm) in plus mode. The full-width-at-half-maximum (FWHM) interval of the slice sensitivity profile 70 is 0.987 mm, which is significantly larger than the native data acquisition detector aperture of 0.625 mm. Approximately 30% of the slice sensitivity profile degradation is caused by the interpolation algorithm used in the cone beam reconstruction process. Approximately 20% of the degradation is due to the "plus" mode of reconstruction where slice sensitivity profile 70 is purposely degraded to reduce image noise and artifacts. Because of the limited frequency response for the CT system, SSP 70 does not exhibit a rectangular shape similar to the detector cell itself. Instead, as shown, the slice sensitivity profile 70 has a smooth, almost Gaussian profile.

Figure 6:
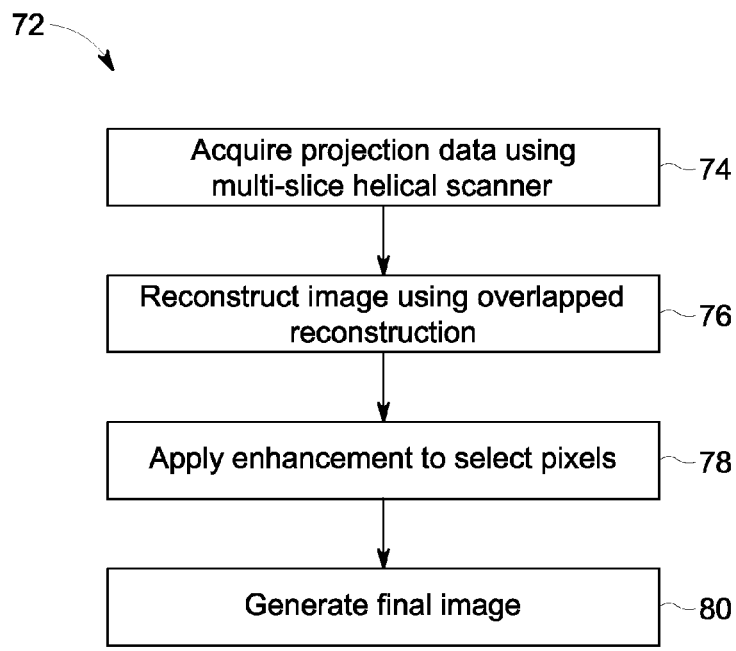
FIG. 6 illustrates a technique for generating an enhanced image, according to an embodiment of the invention

Referring now to FIG. 6, a technique 72 is set forth that reduces the slice sensitivity profile and improves the spatial resolution of the CT scanner without generating the artifacts or noise produced with a known, linear de-convolution algorithm. Technique 72 begins at block 74 by acquiring projection data using a multi-slice CT imaging system, such as CT system 10 (FIG. 1), operating in a helical scan mode. The acquired projection data is reconstructed to generate a set of overlapped initial images at block 76. Overlapped images refer to the fact that the spacing in along the z-axis between adjacent images is smaller than the nominal FWHM of the image slice thickness. Select pixels of the initial image are enhanced in a non-linear manner at block 78 using an iterative algorithm. Technique 72 then uses a combination of enhanced pixel values and non-enhanced pixel values to generate a final image of the object at block 80. The final image may be output to a display, such as display 42 of FIG. 2 to be viewed an analyzed by a user.

Given the smooth varying nature of the slice sensitivity profile of a typical CT system, such as, for example, the slice sensitivity profile illustrated in FIG. 5, any true structure in the object should exhibit similar smooth variation in its intensity profile along the z-axis since the final response of the reconstructed image is simply the convolution of the structure of the object with the slice sensitivity profile. Technique 72 leverages this observation in order to separate real structures in the image from noise-induced fluctuations by analyzing the intensity variation of adjacent pixels along the z-axis. Where the intensity variation of adjacent pixels exhibits a continuous trend, technique 72 assumes that the intensity variations are caused by real structure. However, where the intensity variations do not exhibit a continuous trend, the variations are likely induced by noise. As used herein, the phrase "continuous trend" means that the direction of change of intensity values between adjacent pixels does not reverse direction within a given set of adjacent pixels along the z-axis.

Figure 7:
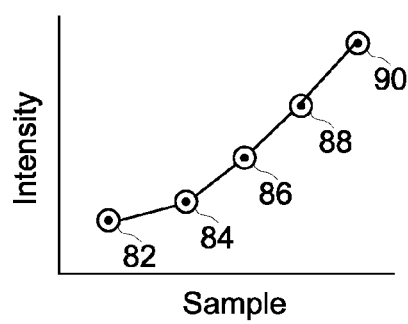
FIG. 7 is a graph illustrating an exemplary intensity variation between pixels corresponding to a group of neighboring sample points along the z-axis.
Figure 8:
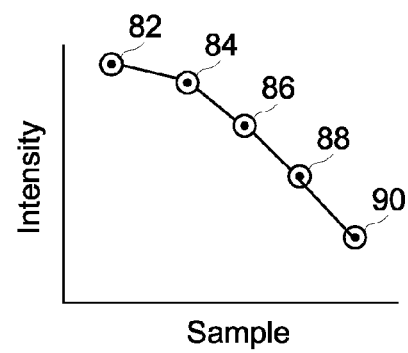
FIG. 8 is a graph illustrating another exemplary intensity variation between pixels corresponding to a group of neighboring sample points along the z-axis.

To analyze the intensity variations, technique 72 evaluates the intensity variation of a group of pixels corresponding to neighboring sampling points along the z-axis. FIGS. 7-10 illustrate four exemplary variations in pixel intensity values between adjacent pixels in a group of neighboring sampling points. If the intensity variation between adjacent pixels within the group exhibits either a continuous ascending trend, as shown in FIG. 7, or a continuous descending trend, as shown in FIG. 8, technique 72 designates a central pixel of the group as a candidate for enhancement because trend in the intensity variation indicates that the central pixel has a high likelihood of corresponding to real structure.

Figure 9:
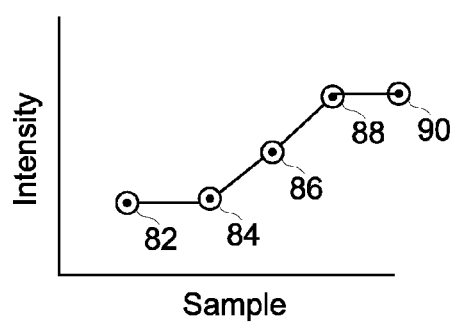
FIG. 9 is a graph illustrating another exemplary intensity variation between pixels corresponding to a group of neighboring sample points along the z-axis.
Figure 10:
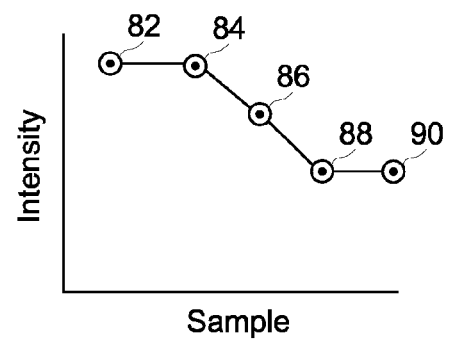
FIG. 10 is a graph illustrating another exemplary intensity variation between pixels corresponding to a group of neighboring sample points along the z-axis.

In some embodiments, technique 72 may also designate a central pixel of the group as an enhancement candidate corresponding to real structure in situations where the centermost pixels of the group of adjacent pixels exhibit a continuous trend and the outlying pixels of the group do not reverse the ascending or descending trend of the centermost pixels, as shown in FIGS. 9 and 10.

In the exemplary embodiments described above, the pixels corresponding to five (5) adjacent sampling points are used to identify a candidate pixel for enhancement. However, the number of sampling points may be varied according to various embodiments based on factors such as, for example, the degree of overlap between images in the overlapped reconstruction, the type of anatomy or object being scanned, the slice thickness, and various other scan parameters.

Technique 72 uses an overlapped reconstruction at block 76 to reconstruct an initial image in order to ensure the pixel samples are collected at fine enough intervals so that adjacent samples that correspond to real structure exhibit the above-described trends in intensity variation between adjacent pixels. That is, if the samples are collected at coarse intervals, very few (if any) central pixels within a group of samples may satisfy the criteria of ascending or descending adjacent pixels even in the case where a sharp edge exists in the scanned object. As such, technique 72 selects the image spacing for the overlapped reconstruction to be smaller than the targeted slice thickness of the original image. As one example, if the original image is acquired and reconstructed to a 0.625 millimeter slice thickness, a 0.1 millimeter spacing may be selected between images. As another example, a 0.2 millimeter spacing between images may be selected if the original image is acquired and reconstructed to a 1.25 millimeter slice thickness. As one skilled in the art will recognize, the image spacing may be optimized to achieve balance between the effectiveness of enhancement candidate identification and the overall speed of the reconstruction.

During the enhancement process, technique 72 calculates the difference between a pixel-of-interest and its neighboring pixels along the z-axis. In the exemplary embodiment where adjacent pixels are analyzed in groups of five samples, for example, the five pixel samples may be designated as $p_{-2}$ 82, $p_{-1}$ 84, $p_0$ 86, $p_1$ 88, and $p_2$ 90, with $p_0$ 86, as the central pixel of the group of samples, being defined as the pixel-of-interest that is analyzed for possible enhancement.

When the central pixel of a given group of samples satisfies any of the conditions illustrated in FIGS. 7-10, the pixel is selected as a candidate for the nonlinear enhancement process. For example, where the intensity of the central pixel, $p_0$, 86 is greater than the intensity of a first adjacent pixel, $p_{-1}$, 84, first adjacent pixel $p_{-1}$ 84 is greater than or equal to the intensity of pixel, $p_{-2}$ 82, the central pixel, $p_0$, 86 is less than the intensity of a second adjacent pixel, $p_1$, 88, and the second adjacent pixel, $p_1$, 88 is less than or equal to pixel $p_2$ 90, as shown in FIGS. 7 and 9, central pixel, $p_0$, 86 is selected as a candidate pixel for enhancement. In these cases, the group of five pixels 82-90 exhibit a continuously ascending trend in intensity. Central pixel, $p_0$, 86 is also selected as a candidate pixel for enhancement when the intensity of the central pixel, $p_0$, 86 is less than the intensity of a first adjacent pixel, $p_{-1}$, 84, first adjacent pixel, $p_{-1}$, 84 is less than or equal to pixel $p_{-2}$ 82, central pixel, $p_0$, 86 is greater than the intensity of a second adjacent pixel, $p_1$, 88, and second adjacent pixel, $p_1$, 88 is greater or equal to pixel $p_2$ 90, as shown in FIGS. 8 and 10. In these cases, the group of five pixels 82-90 exhibit a continuously descending trend in intensity. During the enhancement process, the intensity value of the candidate pixel is iteratively adjusted using a nonlinear enhancement algorithm, as described in detail below.

The enhancement algorithm uses a differential signal, $\Delta$, to calculate the enhancement for a given candidate pixel. The differential signal, $\Delta$, is defined as a negative value according to:

$$\Delta = \begin{cases} p_{-1} - p_o, & \text{ascending trend} \\ p_1 - p_o, & \text{descending trend} \end{cases}. \quad \text{(Eqn. 1)}$$

As indicated in Eqn. 1, differential signal, $\Delta$, is dependent on whether the detected trend in the intensity variations between pixels 82-90 is ascending, as shown in FIGS. 7 and 9, or descending, as shown in FIGS. 8 and 10. Since the differential signal, $\Delta$, is used as the basis for intensity adjustment, the magnitude of the differential signal is selected to be sufficiently small to guard against situations where a large change in intensity may induce undershoot artifacts. Thus, a negative threshold value, $\epsilon$, is used to define the differential signal, $\Delta$, according to:

$$\Delta = \begin{cases} \Delta, & \Delta \geq \varepsilon \\ \varepsilon, & \Delta < \varepsilon \end{cases}. \quad \text{(Eqn. 2)}$$

In one embodiment, the negative threshold value, $\epsilon$, is selected to have a relatively small magnitude based on the iterative enhancement process such as, for example, −20. In alternative embodiments, the negative threshold value, $\epsilon$, may be selected dynamically or adaptively based on past history of the iterative process. For example, the magnitude of the negative threshold value, $\epsilon$, may decrease gradually from iteration to iteration to reflect that each iteration of the enhancement algorithm is moving closer to a final solution.

The amount that the intensity value of a given candidate pixel is adjusted at an iteration k, $\xi_k$, is defined as:

$$\xi_k = \tau_k \cdot w(p_{o,k}) \cdot \Delta_k \cdot e^{-\Delta_k^2 \lambda_k}, \quad \text{(Eqn. 3)}$$

where $\Delta_k$ is the estimated difference at iteration k, $\lambda_k$ is a parameter that controls the amount of adjustment at each iteration, $\tau_k$ is a damping factor, and $w(p_{o,k})$ is a weighting function that controls the amount of correction based on the intensity of the pixel candidate, $p_{0,k}$. Adjustment parameter, $\lambda_k$, may change significantly over iterations. As one example, the adjustment parameters, $\lambda_k$, for a five iteration process may range from an initial value of approximately 0.001 to a final value of approximately 0.0004. The damping factor, $\tau_k$, is selected to control overshoot and undershoot. In one embodiment, $\tau_k$=0.5.

While the parameters described above are effective in separating uncorrelated noise from the real structure in the image, heavily correlated noise may sometime mimic the behavior of the structure. Thus, the weighting function, $w(p_{o,k})$, is used to control potential noise increase in the soft-tissue region due to the enhancement process. In one embodiment, the weighting function, $w(p_{o,k})$, is defined as:

$$w(p_{o,k}) = \begin{cases} 1, & |p_{0,k} - \mu| \geq \alpha \\ |p_{0,k} - \mu|/\alpha, & |p_{0,k} - \mu| < \alpha \end{cases}, \quad \text{(Eqn. 4)}$$

where $\mu$ is the CT number of water ($\mu$=1000), and $\alpha$ is a parameter defining a range of a CT number around water to be affected. Note that in this particular embodiment, the CT value of the entire image is shifted up by 1000 so that the air value is 0 (instead of −1000). In one exemplary embodiment, $\alpha$=80. It should be noted that other formulations can also be used. For example, in one embodiment, $w(p_{o,k})$ can be set to 0 if $|p_{0,k} - \mu| < \alpha$.

The enhanced pixel value, $p_{0,k+1}$, at iteration k+1 is then defined as:

$$p_{0,k+1} = p_{0,k} + \xi_k \quad \text{(Eqn. 5)}.$$

To somewhat conserve the total "mass" in the image, the intensity of at least one of the pixels adjacent to the central pixel (e.g., $p_{-1}$ 84 or $p_1$ 88) is also modified to partially compensate for the reduction in the intensity of the candidate pixel, $p_{0,k}$. For an ascending trend, the intensity of neighboring pixel $p_1$ is increased according to:

$$p_{1,k+1} = p_{1,k} \beta \xi_k \quad \text{(Eqn. 6)},$$

where $\beta$ is a scalar parameter that controls the degree of the "conservation of mass." In one embodiment, $\beta$ has a value of less than one, such as, for example, 0.4. Likewise, for a descending trend, the intensity of neighboring pixel $p_{-1}$ is increased according to:

$$p_{-1,k+1} = p_{-1,k} - \beta \xi_k \quad \text{(Eqn. 7)}.$$

While exemplary values are given above for the various parameters $\lambda$, $\tau$, w, $\alpha$, $\mu$, $\epsilon$, and $\beta$, one skilled in the art will recognize that alternative values for the various parameters of the enhancement algorithm may be selected based on any number of factors, such as, for example, parameters of the imaging system, the composition of the object scanned, desired characteristics of the final image, and the like.

Technique 72 repeats the above-described iterative pixel enhancement process at block 78 by applying the enhancement algorithm to each pixel of the reconstructed image that meets the ascending or descending intensity selection criteria described above and is identified as a candidate pixel. At block 80, technique 72 generates a final image using a combination of the enhanced pixel intensity values for the candidate pixels and pixels adjacent the candidate pixels and the original pixel intensity values for all non-candidate pixels.

Technique 72 is described above as selecting candidate pixels for the enhancement process based on an intensity analysis of a group of neighboring sample points that are immediately adjacent each other along the z-axis. However, in alternative embodiments where the sampling is fine enough, the process for selecting candidate pixels for enhancement may be performed using non-adjacent sample points, such as, for example, groups of pixels representing every other sample point or every third sample point along the z-axis.

In addition, the sampling may be non-uniformly spaced. For example, pixel $p_{-1}$ and pixel $p_1$ are adjacent to pixel $p_0$, but pixel $p_{-2}$ and pixel $p_2$ are spaced 2 or 3 pixels aways from pixel $p_{-1}$ and pixel $p_1$, respectively. The number of samples and their spacing can also be adaptive. For example, in the soft-tissue regions, the number of samples and their spacing can be different than near the bony regions. This is based on the objectives of sharpening up the bony edges or high-density structures. If, on the other hand, the objective is to enhance the iodine-filled vascular structures, the number of samples can be reduced from five (5) to three (3) to account for small vessels. Note that for smaller vascular structures, the rising and trailing edges of the vessel is substantially smaller than the larger vessels. Alternatively, the spacing of the overlapped reconstruction can be smaller. For example, for a 0.625 mm slice thickness reconstruction, the sampling spacing can be set to 0.06 mm. For the enhancement of bigger structures, the overlap spacing can be selected to be 0.2 mm.

In another embodiment, the parameters used in Equation 3 can be selected dynamically based on the characteristics of the imaging region. The number of iterations can be higher than five (5) or the bony regions assuming the objective is to enhance the bones. The parameters $\lambda_k$ can be significantly different than the range of 0.001 to 0.0004 described previously in alternative embodiments.

Similarly, the parameters used in Equation 4 can be selected dynamically based on the task on hand. For example, in embodiments where the objective is to enhance the iodine-filled vascular structures, the formulation of the equation can be modified (note the flip of the larger-than and smaller-than signs):

$$w(p_{o,k}) = \begin{cases} 1, & |p_{0,k} - \mu| \leq \alpha \\ |p_{0,k} - \mu|/\alpha, & |p_{0,k} - \mu| > \alpha \end{cases} \quad \text{(Eqn. 8)}$$

In yet another embodiment of the invention, the acquisition parameters can be adjusted based on the enhancement task on hand. For example, if the goal is to enhance small vascular structures, low-pitch helical acquisition (e.g., pitch=0.5) is used to ensure adequate sampling of the object along the z-axis. Alternatively, variable pitch helical can be used in which the helical pitch is adjusted based on the information provided by the scout.

In yet another embodiment of the invention, the calculation of the differential signal, $\Delta$, in Equation 1 may differ from that described above. For example, instead of using the difference of the center pixel relative to one of its neighbors, the differential signal, $\Delta$, can be calculated based on the weighted average of its two neighbors. The weighting function can be nonlinear depending on the intensity differences of the neighbors. Alternatively, the differential signal, $\Delta$, can also be calculated based on the weighted average of all its neighbors.

In yet another embodiment, Equation 4 can be modified so that w(po,k) changes over more than 3 regions. Note that the current arrange divide the intensity regions into three: one significantly below water, one centered around water, and one significantly above water. In the new embodiment, the entire intensity region can be divided into 5 or more regions. For example, one center around lung tissue, one between lung tissue and water, one centered around water, one between water and bone, and one centered around the bone. Different weighting functions will be applied in different regions.

Figure 11:
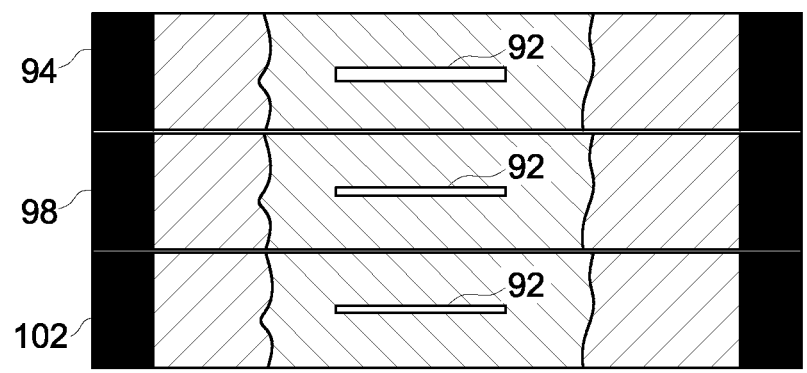
FIG. 11 illustrates exemplary coronal images of a thin foil phantom acquired by a CT imaging system, such as the CT imaging system of FIG. 1, with a targeted slice thickness of 0.625 mm and images reconstructed at 0.1 mm increments.
Figure 12:
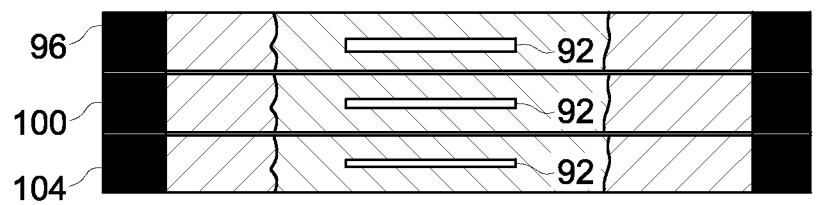
FIG. 12 illustrates exemplary coronal images of a thin foil phantom acquired by a CT imaging system, such as the CT imaging system of FIG. 1, with a targeted slice thickness of 1.25 mm and images reconstructed at 0.2 mm increments.

Referring now to FIGS. 11 and 12, exemplary coronal images of a thin foil phantom 92 acquired in a helical scanning mode are shown to illustrate the effect of the above-described enhancement technique 72, according to various embodiments of the invention. The thin foil phantom illustrated in FIGS. 11 and 12 was built by sandwiching a piece of aluminum foil between two pieces of foam having a density approximately equal to the density of air. The value of the weighting function, $w(p_{o,k})$, is unity in the background region.

FIG. 11 illustrates exemplary coronal images of the reconstructed foil phantom with a targeted 0.625 mm thickness at 0.1 mm spacing with a window width (WW) of 100. FIG. 12 illustrates exemplary coronal images of the reconstructed foil phantom with a targeted 1.2 mm thickness at 0.2 mm spacing (WW=100). A respective top image 94, 96 in each of FIGS. 11 and 12 illustrates the original reconstructed image without any pixel enhancement. Middle images 98, 100 are enhanced images generated using a first set of values for parameters $\epsilon$, $\tau$, $\mu$, w, and the number of iterations in the pixel enhancement technique 72. Likewise, bottom images 102, 104 are the enhanced images generated using a second set of values for parameters $\epsilon$, $\tau$, $\lambda$, w, and the number of iterations in the pixel enhancement technique 72.

Figure 13:
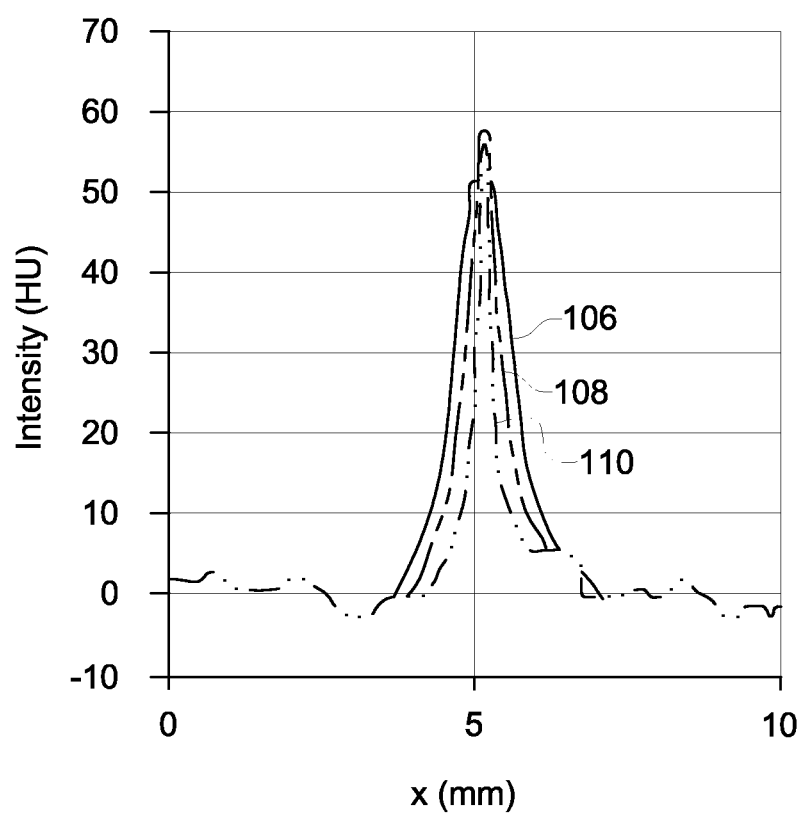
FIG. 13 is a slice sensitivity profile corresponding to the images illustrated in FIG. 11.
Figure 14:
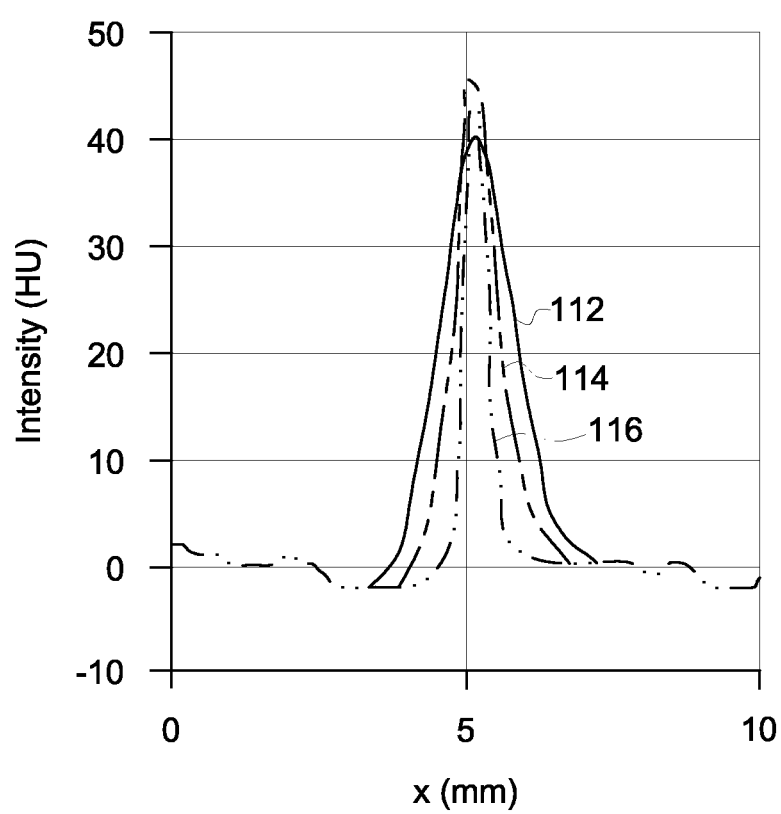
FIG. 14 is a slice sensitivity profile corresponding to the images illustrated in FIG. 12.

FIG. 13 illustrates the corresponding the slice sensitivity profiles for the coronal images of FIG. 11. In particular, slice sensitivity profile 106 corresponds to original top image 94, slice sensitivity profile 108 corresponds to enhanced middle image 98, and slice sensitivity profile 110 corresponds to enhanced bottom image 102 of FIG. 11. FIG. 14 illustrates the corresponding the slice sensitivity profiles for the coronal images of FIG. 12. Slice sensitivity profile 112 corresponds to original top image 96, slice sensitivity profile 114 corresponds to enhanced middle image 100, and slice sensitivity profile 116 corresponds to enhanced bottom image 104 of FIG. 12.

Referring now to FIGS. 11 and 12 with continued reference to FIGS. 13 and 14, the z-axis resolution improvement resulting from use of the pixel enhancement technique clearly illustrated in a comparison of the top images 94, 96 with the middle and bottom images 98-104. That is, the enhanced middle and bottom images 98-104 show a significant improvement in z-resolution as compared to the top images 94, 96. Further, the background of the thin foil 92 is kept nearly untouched by the enhancement algorithm, as shown in FIGS. 11 and 12.

Exemplary FWHM measurements corresponding to the slice sensitivity profiles 112, 114 of FIGS. 13 and 14 are provided in Table 1, below, to further illustrate the improvement in the z-axis resolution resulting from use of the enhancement technique 72.

TABLE 1

| Targeted Slice Thickness | FWHM (original) | FWHM (first parameter set) | FWHM (second parameter set) |
|---|---|---|---|
| 0.625 mm | 0.987 | 0.495 | 0.276 |
| 1.25 mm | 1.409 | 0.861 | 0.537 |

While FIGS. 11 and 12 illustrate the improvements in SSP for an image of a foil phantom generated using enhancement technique 72, using enhancement technique 72 may also be used to generate enhanced anatomical images with improved spatial resolution as compared to an original reconstructed image. For example, enhancement technique 72 may be used to generate an enhanced final image having significantly sharper resolution in bony regions as compared to the original reconstructed image without significantly altering or increasing the noise in the soft-tissue regions. Fuzzy edges present in the original image are significantly reduced in the final enhanced image generated using technique 72. In addition, the enhanced final images generated using enhancement technique 72 are absent overshoot or undershoot artifacts or partial volume artifacts.

Figure 15:
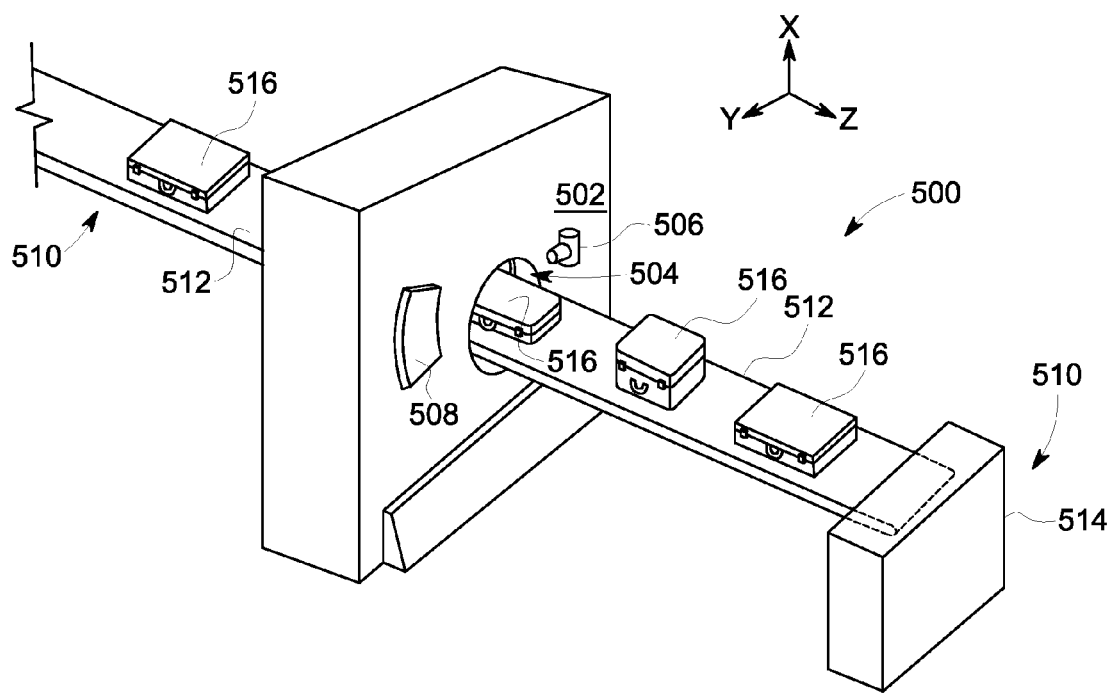
FIG. 15 is a pictorial view of a CT system for use with a non-invasive package inspection system.

Referring now to FIG. 15, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIGS. 3 and 4. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented method of generating an image using a nonlinear enhancement algorithm that iteratively adjusts intensity values of candidate pixels and generates a final image using the adjusted intensity value of the candidate pixel.

Although the above invention describes an algorithmic approach to reduce the slice thickness of the CT system operating in helical mode, it should be understood that similar techniques can be applied to non-helical modes of operation, such as step-and-shoot mode, variable pitch mode, or dynamic shuttle mode. In step-and-shoot mode, the patient remains stationary during the data acquisition. In variable pitch mode, the patient is translated at a variable speed during data acquisition. In dynamic shuttle mode, the patient is translated back-and-forth during acquisition.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not listed may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, a non-transitory computer readable storage medium has stored thereon a computer program comprising instructions, which, when executed by a computer, cause the computer to acquire a set of projections from an object using a CT imaging system and reconstruct an initial image of the scanned object from the set of projections, the reconstructed initial image comprising a plurality of pixels. The instructions also cause the computer to identify a candidate pixel within the plurality of pixels, apply a nonlinear enhancement to the candidate pixel to iteratively adjust an intensity value of the candidate pixel, and generate a final image using the adjusted intensity value of the candidate pixel.

In accordance with another embodiment, a method of generating a CT image includes acquiring CT data representing an object from a CT imaging system, reconstructing a CT image from the acquired CT data, and identifying a set of candidate pixels from the CT image based on an intensity variation between neighboring pixels of the CT image. The method also includes iteratively enhancing an intensity of the set of candidate pixels and generating a final image of the object using the iteratively enhanced set of candidate pixels and a plurality of non-enhanced pixels from the CT image.

In accordance with yet another embodiment, a CT system includes a rotatable gantry having an opening to receive an object to be scanned, an x-ray source positioned on the rotatable gantry and configured to project x-rays at the object, and a multi-slice detector array attached to the gantry and positioned to receive x-rays from the x-ray source that pass through the object. The CT system also includes a table positioned in the opening, the table moveable in a z-direction of the CT system and a computer. The computer is programmed to acquire a plurality of projection datasets of the object, reconstruct an image of the object using the plurality of projection datasets, and identify a plurality of candidate pixels from the reconstructed image based on an intensity variation between a respective candidate pixel of the plurality of candidate pixels and at least two pixels of the reconstructed image adjacent the respective candidate pixel. The computer is further programmed to modify an intensity of the plurality of candidate pixels and generate an enhanced image using the modified intensity of the plurality of candidate pixels.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon a computer program comprising instructions, which, when executed by a computer, cause the computer to:
acquire a set of projections from an object using a computed tomography (CT) imaging system;
reconstruct an initial image of the scanned object from the set of projections, the reconstructed initial image comprising a plurality of pixels;
identify a candidate pixel within the plurality of pixels;
apply a nonlinear enhancement to the candidate pixel to iteratively adjust an intensity value of the candidate pixel; and
generate a final image using the adjusted intensity value of the candidate pixel.

2. The non-transitory computer readable storage medium of claim 1 wherein the instructions further cause the computer to:
identify a group of pixels from the plurality of pixels, the group of pixels comprising adjacent pixels along a z-axis of the CT imaging system;
identify intensity values of the group of pixels; and
select a central pixel of the group of pixels as the candidate pixel if the intensity values continuously increase from a pixel of the group of pixels on a first side of the central pixel to a pixel of the group of pixels on a second side of the central pixel.

3. The non-transitory computer readable storage medium of claim 2 wherein the instructions further cause the computer to define the group of pixels to include at least five adjacent pixels along the z-axis.

4. The non-transitory computer readable storage medium of claim 3 wherein the instructions further cause the computer to select the central pixel of the group of pixels as the candidate pixel if an intensity value of an outer pixel of the group of pixels is equal to an intensity value of a pixel of the group of pixels that is adjacent the outer pixel.

5. The non-transitory computer readable storage medium of claim 2 wherein the instructions further cause the computer to select the central pixel of the group of pixels as the candidate pixel if the intensity values of the adjacent pixels have one of a continuously ascending trend and a continuously descending trend along the z-axis.

6. The non-transitory computer readable storage medium of claim 1 wherein the instructions further cause the computer to:
modify an intensity value of a pixel adjacent the candidate pixel; and
generate the final image using the modified intensity value of the pixel adjacent the candidate pixel.

7. The non-transitory computer readable storage medium of claim 1 wherein the instructions further cause the computer to reconstruct the initial image using an overlapped reconstruction.

8. The non-transitory computer readable storage medium of claim 1 wherein the instructions further cause the computer to acquire the set of projections during a helical scanning mode.

9. A method of generating a computed tomography (CT) image comprising:
acquiring CT data representing an object from a CT imaging system;
reconstructing a CT image from the acquired CT data;
identifying a set of candidate pixels from the CT image based on an intensity variation between neighboring pixels of the CT image;
iteratively enhancing an intensity of the set of candidate pixels; and
generating a final image of the object using the iteratively enhanced set of candidate pixels and a plurality of non-enhanced pixels from the CT image.

10. The method of claim 9 further comprising:
acquiring CT data along a z-axis of the CT imaging system; and
identifying intensity values for respective pixels of a group of neighboring pixels along the z-axis, wherein the group of neighboring pixels comprises a central pixel, a first pixel adjacent the central pixel on a first side of the central pixel, and a second pixel adjacent the central pixel on a second side of the central pixel.

11. The method of claim 10 further comprising identifying the central pixel as a candidate pixel if an intensity value of the central pixel is greater than an intensity value of the first pixel and less than an intensity value of the second pixel.

12. The method of claim 10 further comprising acquiring overlapping sets of CT data along the z-axis.

13. The method of claim 9 further comprising operating the CT imaging system in a helical scanning mode.

14. A computed tomography (CT) system comprising:
a rotatable gantry having an opening to receive an object to be scanned;
an x-ray source positioned on the rotatable gantry and configured to project x-rays at the object;
a multi-slice detector array attached to the gantry and positioned to receive x-rays from the x-ray source that pass through the object;
a table positioned in the opening, the table moveable in a z-direction of the CT system; and
a computer programmed to:
acquire a plurality of projection datasets of the object;
reconstruct an image of the object using the plurality of projection datasets;
identify a plurality of candidate pixels from the reconstructed image based on an intensity variation between a respective candidate pixel of the plurality of candidate pixels and at least two pixels of the reconstructed image adjacent the respective candidate pixel;
modify an intensity of the plurality of candidate pixels; and
generate an enhanced image using the modified intensity of the plurality of candidate pixels.

15. The CT system of claim 14 wherein the computer is further programmed to:
identify a pixel of the reconstructed image as a candidate pixel if an intensity value of the candidate pixel is greater than an intensity value of a first pixel immediately adjacent a first side of the candidate pixel in the z-direction and less than an intensity value of a second pixel immediately adjacent a second side of the respective candidate pixel in the z-direction; and
iteratively modify the intensity of the candidate pixel.

16. The CT system of claim 14 wherein the computer is further programmed to:
- modify an intensity of a pixel adjacent to the respective candidate pixel; and
- generate the enhanced image using the modified intensity of the pixel adjacent to the respective candidate pixel.

17. The CT system of claim 14 wherein the computer is further programmed to:
- acquire the projection dataset during a helical scanning mode of the CT system; and
- use an overlapped reconstruction to reconstruct the image.

18. The CT system of claim 14 wherein a full-width-at-half-maximum (FWHM) of a slice sensitivity profile of the reconstructed image is greater than a FWHM of a slice sensitivity profile of the enhanced image.

19. The CT system of claim 14 wherein the computer is further programmed to reconstruct the image at a slice thickness of 0.625 millimeters and an image spacing of 0.1 millimeters.

20. The CT system of claim 14 wherein the computer is further programmed to reconstruct the image at a slice thickness of 1.25 millimeters and an image spacing of 0.2 millimeters.

\* \* \* \* \*